(12) United States Patent
Vinikova et al.

(10) Patent No.: US 6,319,952 B1
(45) Date of Patent: Nov. 20, 2001

(54) COMPOSITIONS AND METHODS FOR REVERSIBLY INCREASING PERMEABILITY OF BIOMEMBRANES

(75) Inventors: Marina Vinikova; Israel Shapiro, both of Ramla; Alexander Kozak, Rehovot, all of (IL)

(73) Assignee: D-Pharm Ltd., Rehovot (IL)

( * ) Notice: Subject to any disclaimer, the term of this patent is extended or adjusted under 35 U.S.C. 154(b) by 0 days.

(21) Appl. No.: 09/462,532
(22) PCT Filed: Jul. 7, 1998
(86) PCT No.: PCT/IL98/00317
§ 371 Date: Apr. 10, 2000
§ 102(e) Date: Apr. 10, 2000
(87) PCT Pub. No.: WO99/02120
PCT Pub. Date: Jan. 21, 1999

(30) Foreign Application Priority Data
Jul. 9, 1997 (IL) .................................................. 121269

(51) Int. Cl.⁷ .............................. A61N 37/18; A61K 31/16
(52) U.S. Cl. ................................ 514/613; 554/35; 554/79
(58) Field of Search ........................ 554/35, 29; 514/613

(56) References Cited

U.S. PATENT DOCUMENTS

| | | |
|---|---|---|
| 4,846,991 | 7/1989 | Suzue et al. .................. 252/89.1 |
| 5,278,300 | 1/1994 | Hasegawa et al. .............. 536/53 |

FOREIGN PATENT DOCUMENTS 0632008   1/1995   (EP) ........................... C07C/53/50

OTHER PUBLICATIONS

Chem. Abstr., 125:338721, 1996.*
Chemical Abstracts: vol. 126, No. 8, Feb. 24, 1997, p. 1018, col. 2, abstract No. 108640t, Jacob et al., "Branched Carboxylic Acid Esters as Antibacterial, Antifungal, and Antiviral Agents."
Chemical Abstracts: vol. 122, No. 13, Mar. 27, 1995, p. 948, col. 2, abstract No. 160096b, Ohuchida et al., "Preparation of Valprate Analogs as Neuroprotectants."

* cited by examiner

*Primary Examiner*—Deborah D. Carr
(74) *Attorney, Agent, or Firm*—Davidson, Davidson & Kappel, LLC

(57) ABSTRACT

The present invention provides a family of branched fatty acids and their derivatives, which improve and enable the penetration and absorption of active ingredients through biomembranes, such as blood brain barrier. The invention further provides pharmaceutical compositions comprising these branched fatty acids and methods of using these compositions to permeabilize biological membranes thereby improving the administration of bioactive or therapeutic substances to cells or organs. According to a more preferred embodiment of this invention the methods are particularly useful to treat certain kinds of CNS lesions and diseases including tumors, infections, abscesses and degenerative and behavioral disorders.

44 Claims, 11 Drawing Sheets

ALBUMIN CLEARANCE AT 180 MINUTES
1 HR WITH DP-BFA

CLEARANCE ALBUMIN DP-BFA 1HR

LDH IHR WITH DP-BFA
(ALBUMIN PERMEABILITY)

INULIN CLEARANCE AT 45 MINUTES
IHRS WITH DP-BFA
+24HRS REVERSIBILITY (R)

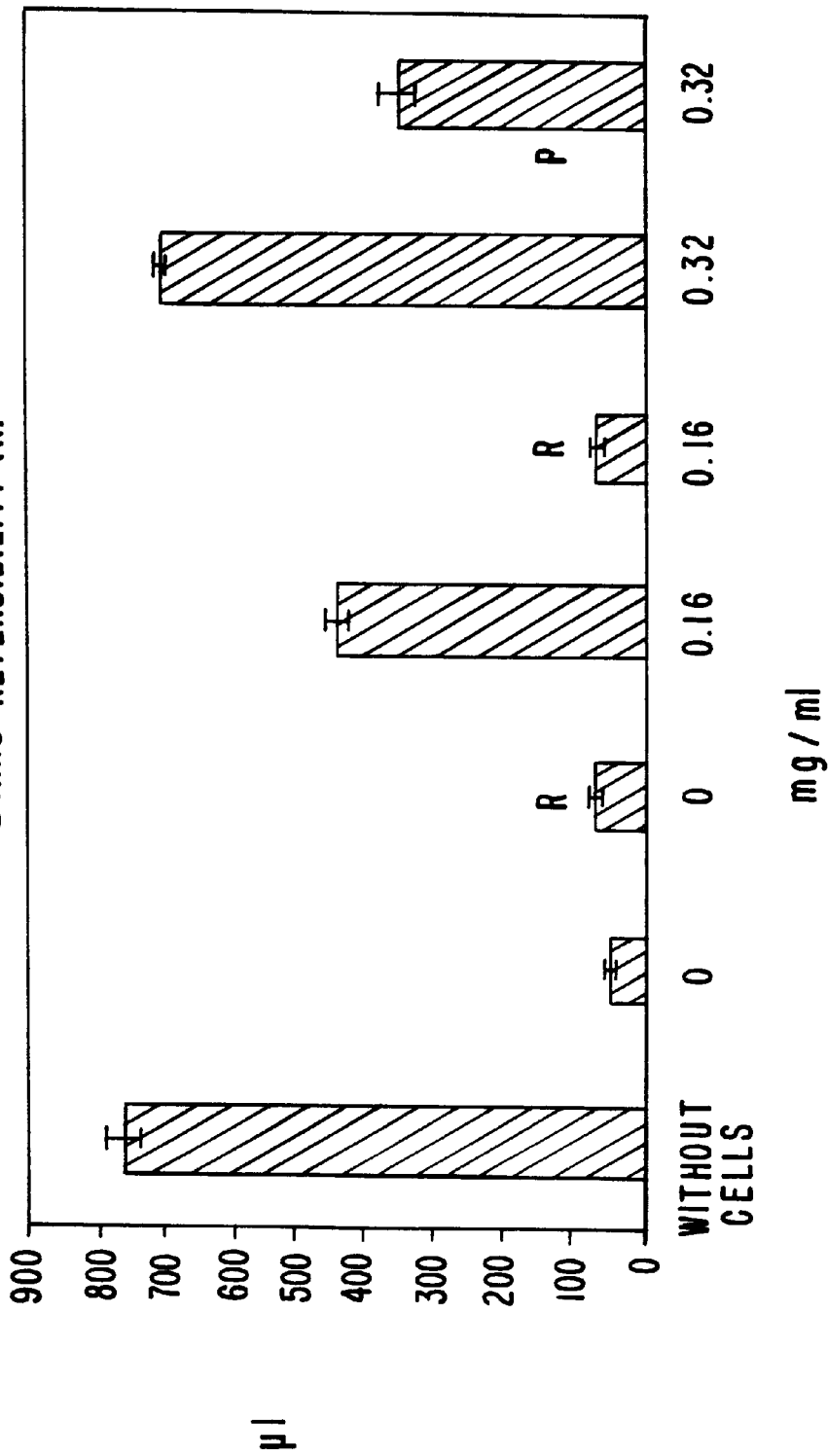

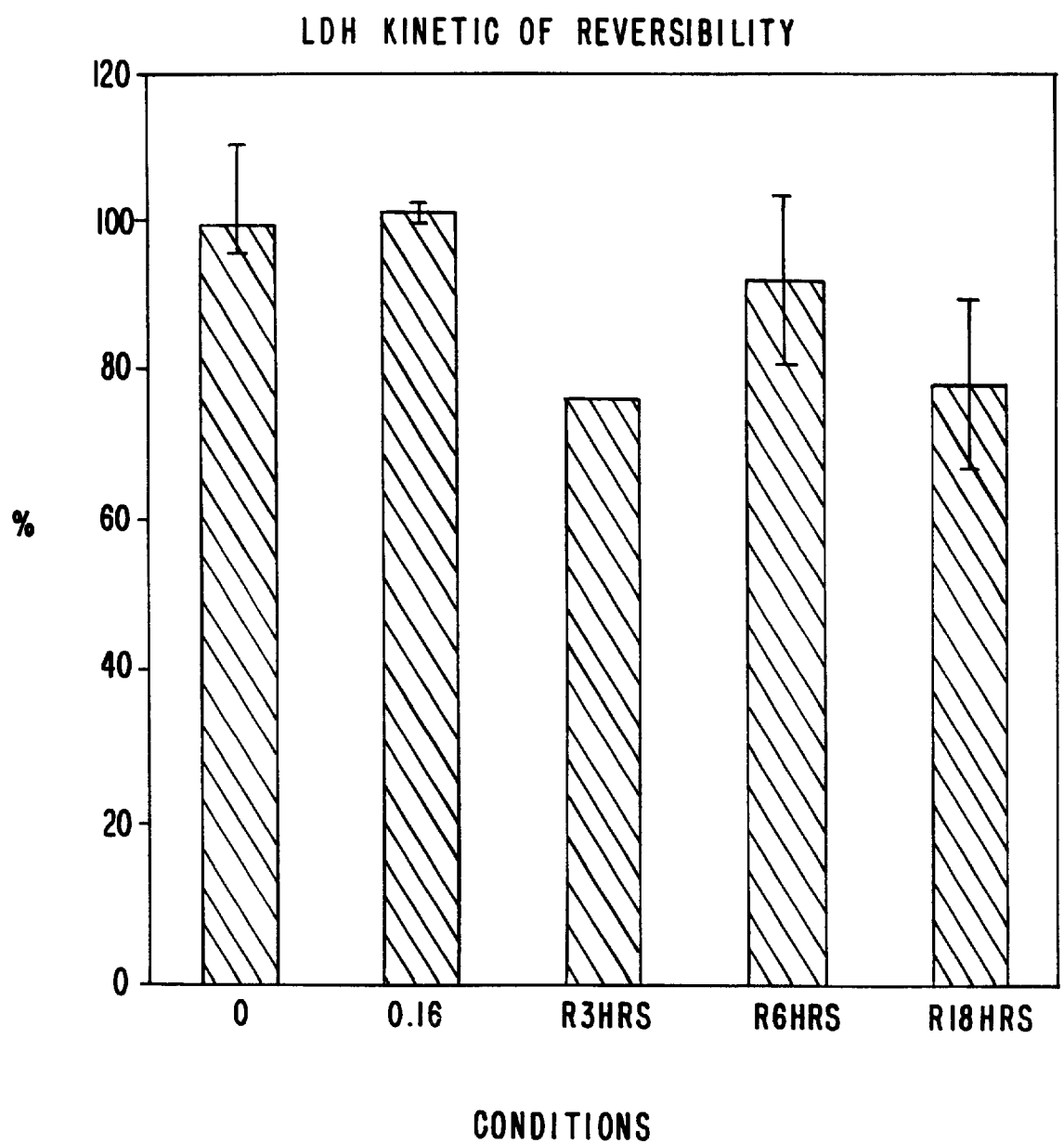

COMPOSITIONS AND METHODS FOR REVERSIBLY INCREASING PERMEABILITY OF BIOMEMBRANES

This application is a 371 of PCT/IL98/08317 filed Jul. 7, 1998.

FIELD OF THE INVENTION

The present invention relates to branched chain fatty acids and their derivatives, useful to facilitate or enable the penetration or transport of active ingredients through biomembranes, including the blood brain barrier, to pharmaceutical compositions comprising these fatty acids and to methods of using them to treat central nervous system lesions including tumors, infections, abscesses and degenerative disorders.

BACKGROUND OF THE INVENTION

It has long been recognized that there is a need for agents which can improve or enable the permeability of non-lipophilic bioactive substances through biomembranes. In particular it would be advantageous to have agents that permit the reversible or transient permeabilization of biomembranes, such that bioactive molecules can be transported into cells or organs that are not normally accessible to these molecules without adversely affecting the viability of the cells. By way of example, the transport of nucleic acids and many other non-lipophilic substances is hampered by the lipophilic barrier that constitutes the cell membrane. There is an even greater need for agents that would enable therapeutic molecules to cross the lipophilic barrier that constitutes the blood brain barrier.

In the normal situation the central nervous system (CNS) is separated by a barrier from the general circulation, thereby permitting rigorous control of the microenvironment required for complex neural signaling. In certain pathological situations this blood brain barrier (BBB) interferes with the transport of therapeutic substances into the brain, thus hampering treatment of central nervous system lesions, including tumors, infections, abscesses and degenerative diseases.

The BBB maintains the homeostatic environment of the brain so that it can function irrespective of fluctuations in the systemic concentrations of compounds in the body. Moreover, it protects the brain from toxic agents and degradation products present in the circulatory system. Paradoxically, this barrier, which normally protects the brain, may be the cause for inefficient drug delivery into the brain, though in the pathological situation drug availability is crucial.

Molecules that show high therapeutic value in vitro and ex vivo in treatment of malignant infections and genetic diseases of the central nervous system are frequently found to be inactive in-vivo. This effect is due to insufficient access of the agent to the diseased target. Treatment of brain tumors is therefore problematic and the patients have poor prognoses. The same diminished effect can be seen in treatment of acute cerebral bacterial and viral infections, as well as with neurodegenerative and enzyme-deficiency diseases, such as Parkinson's disease, Huntington's chorea and Tay-Sachs disease.

Theoretically, the bioavailability problem presented above can be dealt with in several ways. The problem of delivering water soluble compounds, and in particular anti-cancer drugs, can be overcome by altering the biophysical characteristics of the drug. The permeability of a drug depends on its lipophilicity; thus, increasing the lipophilic nature of the compound may increase the therapeutic effect. Modification of a hydrophilic drug with hydrophobic groups such as alkyl or aromatic groups is a common way to improve their bioavailability. However, not all drugs maintain their therapeutic value after chemical modification.

Another strategy for attacking the problem of BBB impermeability is to alter the BBB itself, to enable transportation of the therapeutic substance into the brain (reviewed by Abbott and Romero, Molecular Medicine Today, March 1996, pp. 106–113). The most conmmon method of opening the BBB is by osmotic treatment. Mannitol is in clinical use as an agent for osmotic modification of the BBB. It was shown that chemotherapy administrated after barrier opening results in enhanced drug entry to both brain-tumor and brain, however, the studies also showed evidence that osmotic BBB modification causes complications. The primary problems include clinical manifestation of stroke, seizures, immunological reaction and ocular toxicity. Moreover, the osmotic treatment affects BBB opening for a very short period (Greig in Implications of the Blood-Brain Barrier and its Manipulation. Vol. 1, pp. 311–367, Neuwelt, E. A. ed., Plenum Press, N.Y., 1989).

A variety of other treatments have also been disclosed that increase permeability of the blood brain barrier including: the use of bradykinin agonists (WO 91/16355 of Alkermes) and certain other peptides (WO 92/18529 of Alkermes); use of bacterial cell wall fragments (WO 91/16064 of the Rockefeller Univ.) or the use of antibody to Bordetella pertussis filamentous haemagglutinin or brain endothelial x-molecule (WO 92/19269 of the Rockefeller Univ.). Certain fatty acids such as oleic acid have also been reported to reversibly open the BBB (Sztriha and Betz, Brain Res. 336, 257–262, 1991).

It has also been shown that valproic acid and other short chain fatty acids have membrane disordering potency and it was proposed that this activity might be correlated with the known sedative and anti-convulsant activity of these compounds (Perlman and Goldstein, Mol. Pharmacol. 26, 83–89, 1984).

The usefulness of methods for reversibly increasing the permeability of the blood brain barrier prior to administration of diagnostic reagents (U.S. Pat. No. 5,059,415 of the Oregon Health Sci. U.) or therapeutic reagents (WO 89/11299 of the Oregon Health Sci. U.) have been disclosed.

Known compositions for the permeabilization of biological membranes have not gained widespread acceptance in the medical community due to their adverse side effects or to their very short duration of action. Clearly, there is an unmet medical need for less toxic treatments with longer duration of action that will enable known effective drugs or diagnostic reagents to penetrate into the brain.

SUMMARY OF THE INVENTION

The present invention provides a family of branched fatty acids and their derivatives, which improve and enable the penetration and transport of active ingredients through biomembranes. The invention further provides pharmaceutical compositions comprising these branched fatty acids and methods of using these compositions to permeabilize biological membranes thereby improving the administration of bioactive or therapeutic substances to cells or organs. According to a more preferred embodiment of this invention the methods are particularly useful to treat certain kinds of CNS lesions and diseases including but not limited to tumors, infections, abscesses and degenerative or behavioral disorders.

According to one aspect of the invention certain novel compounds are provided of general formula I:

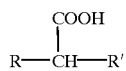

(I)

wherein R denotes a saturated or unsaturated chain of between 3 to 10 carbon atoms and R' denotes a saturated or unsaturated chain of between 10 and 30 carbon atoms, their salts esters and amides.

The present invention further provides pharmaceutical compositions for permeabilization of biological membranes comprising a pharmaceutically effective amount of a branched fatty acid of the general formula II:

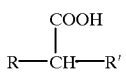

(II)

wherein R denotes a saturated or unsaturated chain of between 1 to 10 carbon atoms and R' denotes a saturated or unsaturated chain of between 5 and 30 carbon atoms, their salts esters and amides.

Currently more preferred compositions according to the present invention comprise a compound selected from the group consisting of:

2-propyldodecanoic acid (denoted herein as M3/10)
2-propyltetradecanoic acid (denoted herein as M3/12)
2-propylhexadecanoic acid (denoted herein as M3/14)
2-heptylnonanoic acid (denoted herein as M7/7)
2-heptyldodecanoic acid (denoted herein as M7/10)
2-heptylhexadecanoic acid (denoted herein as M7/14)
2-decanyldodecanoic acid (denoted herein as M10/10)
2-decanylhexadecanoic acid (denoted herein as M10/14)
2-tetradecanylhexadecanoic acid (denoted herein as M14/14)

Within the scope of the p invention the fatty acids may be used as free carboxylic acids or their physiologically acceptable salts, esters and amides. More preferred pharmaceutical compositions according to the present invention comprise a pharmaceutically effective amount of a compound of the general formula III:

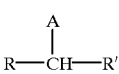

(III)

wherein R denotes a saturated or unsaturated chain of between 1 to 10 carbon atoms and R' denotes a saturated or unsaturated chain of between 5 and 30 carbon atoms, and A is selected from the group consisting of COOH, COOR", $CONH_2$, CONH—R", and $COO^-Y^+$
wherein R" is a lower alkyl group comprising 1–5 carbon atoms, and Y denotes any pharmaceutically acceptable counter-ion.

In further embodiments of the present invention pharmaceutical compositions according to the present invention will further comprise carriers and diluents providing physiologically acceptable formulations including but not limited to aqueous solutions, micelles, cosolvent solutions, emulsions and complexes with amorphous cyclodextrins.

The present invention further provides methods of manufacturing a medicament for the permeabilization of biological membranes comprising the step of placing a pharmaceutically effective amount of a compound in a pharmaceutically acceptable carrier, the compound being of the general formula II:

(II)

wherein R denotes a saturated or unsaturated chain of between 1 to 10 carbon atoms and R' denotes a saturated or unsaturated chain of between 5 and 30 carbon atoms, their salts esters and amides.

The present invention further provides methods of manufacturing a medicament for the permeabilization of biological membranes comprising the step of placing a pharmaceutically effective amount of a compound in a pharmaceutically acceptable carrier, the compound being of the general formula III, as heretofore defined.

In further embodiments of the present invention methods are provided for permeabilizing biological membranes comprising the step of exposing the membranes to a compound of the general formulae II or III, as heretofore defined.

According to a more preferred embodiment of the present invention the pharmaceutical compositions comprising compounds of the general formula II and III are useful as premedication to facilitate the penetration or absorption of therapeutic or diagnostic agents into the central nervous system.

A further embodiment according to the present invention provides methods of treating CNS lesions and diseases comprising: administering to a subject in need thereof a pharmaceutical composition comprising a pharmaceutically effective amount of a compound of the general formula II or III as heretofore defined; and subsequently administering a therapeutic agent within 24 hours.

A yet further embodiment of the present invention provides methods of improving CNS imaging comprising: administering to a subject in need thereof a pharmaceutical composition comprising a pharmaceutically effective amount of a compound of the general formula II or III as heretofore defined; and subsequently administering a CNS imaging agent within 24 hours.

The pharmaceutical compositions will be administered by parenteral routes of administration, preferably intravenous, more preferably intra-arterially, most preferably into the carotid artery.

BRIEF DESCRIPTION OF THE FIGURES

FIG. 9: Sucrose clearance (μl) at 45 minutes, after 24 hrs reversibility
FIG. 13: Determination of LDH in the medium of endothelial cells in coculture

DETAILED DESCRIPTION OF THE INVENTION

Figure 1:
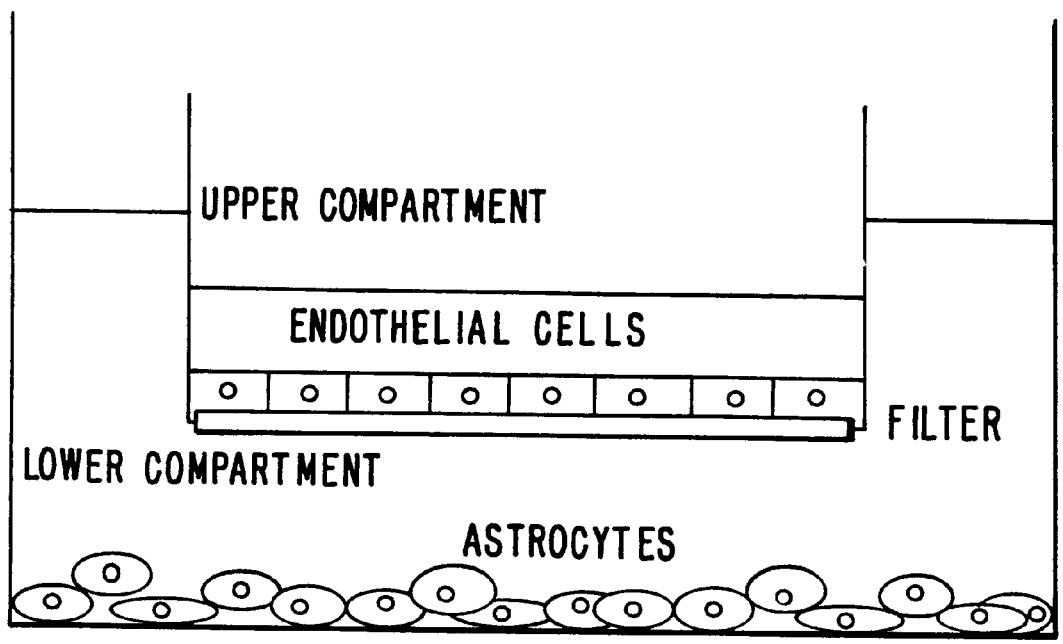
FIG. 1: Scheme of the coculture

According to the present invention it is now disclosed that certain branched fatty acids of the general formulae I and II as heretofore defined have useful properties that enable or increase the penetration of biologically active molecules through biomembranes.

Compositions according to the present invention are useful for facilitating the reversible permeabilization of biological membranes. They can be used as tools for the effective transport of molecules through the cell membrane. More preferably they can be used in vivo for the transport of molecules into cells or organs. Most preferably they can be used for the facilitation of transport of therapeutic molecules through the blood brain barrier.

The fatty acids of the present invention may be saturated or unsaturated. The saturated branched fatty acids according to the present invention are also known as 2-alkyl fatty acids or dialkyl acetic acids or 2-alkylalkanoic acids or 2-alkylalkanoates.

The compounds of the present invention may be utilized as aqueous solutions of the salts or as esters and amides. The free carboxylic acids may also be used after suitable formulation as is known in the art for lipophilic substances. Suitable formulations include, but are not limited to incorporation of the compounds into emulsions, micelles, cosolvent solutions, complexation with cyclodextrins and the like. In vivo the compositions will be administered parenterally, the preferable route of administration being intravenously, more preferably intra-arterially, most preferably into the carotid artery. When used as a treatment facilitating the penetration of therapeutic or diagnostic agents into the brain the composition will be administered to the subject prior to the administration of the agent. Depending on the dose and route of administration the desired action of the composition of the invention in disrupting the BBB may last for a number of minutes or hours.

The synthesis of dialkyl acetic acids such as the branched fatty acids of the present invention is generally based on well known principles of organic chemistry. By way of example the synthesis of 2-ethylpentanoic acid from diethyl malonate is described in a textbook of organic chemistry (Organic Chemistry by. Graham Solomons IV edition John Wiley & Sons, Inc. 956–958).

Some of the molecules that are used according to the present invention are novel chemical entities and are claimed as such, while some were reported for other uses. For example two molecules of M3/14 (2-propylhexadecanoic acid) were attached to glycero-3-phosphatidyl choline at positions 1 and 2 in studies on non-natural phospholipids (Lewis et al. 1994 Biophys. J. 66 1088–1103). In addition, as mentioned previously, some valproic acid analogs were synthesized and characterized in terms of their anti-convulsant or antiepileptic activity (Perlman and Goldstein, 1984 ibid.).

In contradistinction to previously disclosed compositions that are useful for the transient or reversible permeabilization of biological membranes the compositions of the present invention show low toxicity. Moreover, depending on the route of administration, the dose administered and the particular compound used the duration of disruption of the biomembranes can be optimized. As will be exemplified hereinbelow, it may last only several hours or as long as in excess of 24 hours. According to the use that is required the skilled artisan will be able to adjust the compositions of the present invention in order to obtain the desired duration and degree of action.

The present invention will be exemplified in terms of the following non-limitative examples and currently preferred embodiments.

EXAMPLES

I. Synthetic Examples

The synthesis of 2-alkyl fatty acids also known as dialkyl acetic acids is generically accomplished by a four-stage procedure, which will be exemplified herein in the detailed of the synthesis of 2-propylhexadecanoic acid.

Alkylation of diethyl ester of malonic acid is the first stage.

The second stage is alkylation of diethyl propylmalonate.

Hydrolysis of diethyl ester of dialkylmalonic acid is the third stage.

The final product is prepared by decarboxylation of the corresponding dialkylmalonic acid.

Stage 1
Synthesis of Diethyl Propylmalonate $$CH_2(CO_2C_2H_5)_2 + NaH \rightarrow NaCH(CO_2C_2H_5)_2 + H_2 \qquad 1.$$

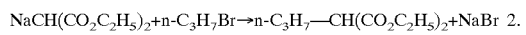

$$NaCH(CO_2C_2H_5)_2 + n\text{-}C_3H_7Br \rightarrow n\text{-}C_3H_7\text{---}CH(CO_2C_2H_5)_2 + NaBr \qquad 2.$$

Sodium hydride (8.25 gr., 0.344 Mol) under argon is introduced into a two-neck flask (1 L), equipped with a magnetic stirrer and a reverse condenser (water cooling). Also under argon tetrahydrofuran (THF, 100 ml) is introduced into the flask. THF is freshly distilled under $LiAlH_4$. The drop funnel is joined to the flask and the solution of diethyl malonate (47.4 ml, 0.312 Mol) in THF (150 ml) is added drop-by-drop to the mixture of NaH with THF. The mixture is stirred by magnetic stirrer during drip, and for some time thereafter until hydrogen bubbles evolve from the mixture. Then a solution of propyl bromide (28.4 ml, 0.313 Mol) in THF (50 ml) is added drop-by-drop. In order to complete the reaction the mixture is heated at 80–90° C. After 5 hours the mixture is cooled down to room temperature and the unreacted sodium hydride is decomposed by ethanol (50 ml). The precipitate is filtered and the obtained solution is evaporated under vacuum (about 25 mm Hg). The rest is dissolved in petroleum ether (200 ml) and this solution is washed three times by water (each portion is 100 ml) in a separated funnel. The organic phase is dried by $MgSO_4$ for 8 hours and petroleum ether is distilled under vacuum. Yield of diethyl propylmalonate is 50.5 gr (0.250 Mol).

TLC analysis: Silica gel 60 $F_{254}$ on aluminum sheet. Eluent is mixture from petroleum ether with diethyl ether (9:1 v/v). Chromatogram is sprinkled by indicator spray and then is charred at 150° C. Composition of indicator spray: 4-methoxybenzaldehyde (10 ml), ethanol (200 ml), 98% $H_2SO_4$ (10 ml) and glacial acetic acid (2 ml). One spot. $R_f$ 0.54.

Stage II
Synthesis of Diethyltetradecylmalonate

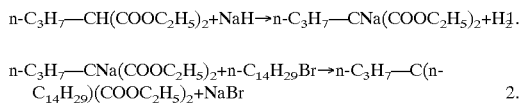

$$\text{n-C}_3\text{H}_7\text{—CH(COOC}_2\text{H}_5)_2 + \text{NaH} \rightarrow \text{n-C}_3\text{H}_7\text{—CNa(COOC}_2\text{H}_5)_2 + \text{H}_2. \quad 5$$

$$\text{n-C}_3\text{H}_7\text{—CNa(COOC}_2\text{H}_5)_2 + \text{n-C}_{14}\text{H}_{29}\text{Br} \rightarrow \text{n-C}_3\text{H}_7\text{—C(n-C}_{14}\text{H}_{29})(\text{COOC}_2\text{H}_5)_2 + \text{NaBr} \quad 2.$$

Sodium hydride (6.6 g., 0.275 Mol) under argon is introduced into a round-bottom double-neck flask (1 L), equipped with magnetic stirrer and a reverse condenser (water cooling). Under argon 150 ml of THF is introduced into the flask. The drop funnel is joined to the flask and the solution of diethyl propylmalonate (50.5 g., 0.250 Mol) in 150 ml of THF is added drop-by-drop to the mixture of NaH with THF. The mixture is stirred with a magnetic stirrer. When the emission of hydrogen bubbles from the reaction mixture stops, the drop funnel with the solution of tetradecylbromide (69.0 g., 0.250 Mol) in 150 ml of THF is joined to the flask and this solution is introduced drop-by-drop into the reaction mixture. The reaction mixture is heated for 5 hours at 90° C. Then the flask is cooled down to room temperature and the unreacted sodium hydride is decomposed using ethanol (50 ml). The resulting solution is evaporated under vacuum (about 40 mm Hg). About 500 ml of petroleum ether is added to the residue and this solution is washed 3 times with water (every portion is 150 ml). The organic solution is dried with $MgSO_4$ and the solvent is evaporated under vacuum (30 mm Hg). The obtained raw product is purified by column chromatography. For purification of 1 g. of raw product we used 40 g. of silica gel 60 (70–230 mesh), eluent is a solution of petroleum ether (97%) with diethyl ether (3%). The yield of diethyl propyltetradecylmalonate is 50% (45 g.).

TLC analysis: Silica gel 60 $F_{254}$ on an aluminum sheet. Eluent is a mixture of petroleum ether with diethyl ether (9:1 v/v). Chromatogram is sprayed by indicator spray and then is burned at 350° C. Composition of indicator spray see stage I. One spot. $R_f$ 0.54.

Stage III
Hydrolysis of Diethyl Propyltetradecylmalonate

$$\text{n-C}_3\text{H}_7\text{—C(C}_{14}\text{H}_{29})(\text{COOC}_2\text{H}_5)_2 + 2\text{H}_2\text{O} \rightarrow \text{n-C}_3\text{H}_7\text{—C(n-C}_{14}\text{H}_{29})(\text{COOH})_2 + 2\text{C}_2\text{H}_5\text{OH}$$

Diethyl propyltetradecylmalonate (45 g., 0.116 Mol), potassium hydroxide (40 g., 0.696 Mol), water (40 ml) and ethanol (80 ml) are introduced into a round-bottom single-neck flask (250 ml), equipped with a magnetic stirrer and a reverse condenser. The reaction mixture is heated in an oil bath for 4 hours at 90° C. Then the reaction is cooled down to room temperature and the mixture is transferred into a separated funnel. The unreacted diethyl propyltetradecylmalonate is extracted with petroleum ether (three portions, each portion is 100 ml). The remaining water solution is cooled with ice and then is acidified by concentrated hydrochloric acid up to pH 1–2. The obtained propyltetradecylmalonic acid is extracted by chloroform (three times, each portion is 100 ml) and is dried by $MgSO_4$. Chloroform is evaporated under vacuum (25 mm Hg). Yield of propyltetradecylmalonic acid is 90% (36 g.)

TLC analysis: Silica gel 60 $F_{254}$ on aluminum sheet. Eluent is mixture of chloroform with methanol (95:5 v/v). Chromatogram is sprayed by indicator spray and is charred at 150° C. For composition of indicator spray see stage I. One spot. $R_f$ 0.05.

Stage IV
Decarboxylation of Propyltetramalonic Acid

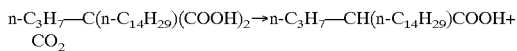

$$\text{n-C}_3\text{H}_7\text{—C(n-C}_{14}\text{H}_{29})(\text{COOH})_2 \rightarrow \text{n-C}_3\text{H}_7\text{—CH(n-C}_{14}\text{H}_{29})\text{COOH} + \text{CO}_2$$

Propyltetradecylmalonic acid (36.0 g., 0.104 Mol) is introduced into a single-neck round-bottom flask (150 ml) and is heated in an oil bath at 160–170° C. until $CO_2$ bubbles are no longer visible. For completion of the reaction, the flask is joined to a vacuum (40 mm Hg) and heated at 120° C. for 1 hour. The obtained 2-propyl hexadecanoic acid is purified by column chromatography. For purification of 1 g of raw product we used 40 g. of silica gel 60 (70–230 mesh). The eluent is a mixture of chloroform with methanol (97:3 v/v). After chromatographic purification we obtained a white solid product. m.p. 41.2° C.

Analysis. TLC. Silica gel 60 $F_{254}$ on aluminum sheet. Eluent is a mixture of chloroform with methanol (95:5 v/v). Chromatogram is sprayed by indicator spray and is charred at 150° C. For composition of indicator spray see stage I. One spot. $R_f$ 0.55.

Elementary analyses. $C_{19}H_{38}O_2$. Calculated: C, 76.51%, H, 12.75%. Found: C, 76.19%, H, 13.55%.

$^1$H NMR ($CDCL_3$), $\delta$(ppm): 0.85–0.97 (m. 6H), 1.30 (broad s. 26H), 1.33–1.50 (m.2H), 1.59–1.65 (m. 2H) and 2.36 (m. 1H).

The procedure for preparation of other 2-alkyl fatty acids is analogous to synthesis of 2-propyl hexadecanoic acid.

II. Physiological Examples

Evaluation of Effect of Branched Fatty Acids on Blood-brain Barrier Permeability The experiments were carried out on male Sprague-Dawley rats weighing 250–320 gr. They were anesthetized with Rampun-Imalgen. The right common carotid artery was exposed. The occipital, superior thyroid arteries were ligated and the right external carotid artery was catheterized for retrograde infusion.

The test compounds were dissolved in 0.1M phosphate buffered physiological saline (pH=7.4) at the following test concentrations: 1.6; 8; 20; 40; 200 and 1000 μg/ml. The highest dose (1000 μg/ml) was observed to form micelles. The resulting pH of the test solutions was in the range of 8.0 to 8.5, and contols for the pH effect were performed up to pH 9.

The test compound was infused into the right common carotid artery at a rate of 6 ml/min. for 30 s. The control rats were infused with buffer. Evan's Blue (EB) solution at a concentration of 4 mg/kg body weight (2 g Evan's Blue, 0.9 g NaCl in 100 ml water) was injected intravenously 50 minutes prior to the termination of the experiment.

In the case of 45 min experiment, five minutes prior to the infusion of the tested material, 4 ml/kg body wt dose of Evans Blue solution was injected intravenously.

At the end of the experimental time period the animals were perfused with 100 ml of saline solution through the heart and decapitated. The degree of BBB opening, in terms of extravasation of Evan's Blue albumin, was graded on the basis of visual assessment of the degree of staining of the brain ato the method of Rapoport et al. (Rapoport et al., 1980, Amer. J. Physiol. 258, 421–431), and the results are presented in Tables 1 and 2.

TABLE 1

Effect of different branched chain fatty acids on BBB permeability by qualitative EB evaluation in rats

| Group | Concentration μg/ml | Concentration μM | Time, min | Visual EB |
|---|---|---|---|---|
| M3/3 | 100 | 625 | 45 | − |
| M 3/7 | 139 | 625 | 45 | − |
| M 3/10 | 165 | 625 | 45 | ++ |
| M 10/10 | 226 | 625 | 45 | ++ |
| M 3/14 | 200 | 625 | 45 | +++ |
| M 3/14 | 40 | 125 | 180 | ++ |
| M 3/12 | 30 | 125 | 180 | ++ |
| oleic acid | 40 | 125 | 180 | − |

The results presented are qualitative with four degrees of Evan's Blue extravasation according to Rapoport et al. Minus signs represents no staining and three plus signs represent maximal staining.

The results show that M3/14 was the most potent BBB permeability enhancer. The effect is dose dependent as can be seen in Table 2.

TABLE 2

Dose dependent effect of M 3/14 on BBB permeability in vivo

| Group | Concentration μg/ml | Conc. μM/ml | Time, min | Visual EB |
|---|---|---|---|---|
| Control | | | 180 | − |
| M 3/14 | 1.6 | 5 | 180 | − |
| M 3/14 | 8 | 25 | 180 | + |
| M 3/14 | 20 | 62.5 | 180 | + |
| M 3/14 | 40 | 125 | 180 | ++ |
| M 3/14 | 40 | 125 | 45 | ++ |
| M 3/14 | 200 | 625 | 45 | +++ |
| M 3/14 | 1000 | 3125 | 45 | +++ |

The results presented are qualitative with four degrees of Evan's Blue extravasation according to Rapoport et al. Minus signs represents no staining and three plus signs represent maximal staining.

A second set of experiments was designed to determine whether the BBB disruption is reversible or irreversible after M 3/14 injection. The extravasation of Evan's Blue-albumin was evaluated at different time points between 3 h and 72 h after M 3/14 injection in concentrations of 8 and 20 μg/ml. As shown in Table 3, depending on the dose used, the effect of this compound may exceed 24 hours.

TABLE 3

Reversibility of effect of M 3/14 on BBB permeability

| Group | Concentration (μg/ml) | Time | Quantity EB (absorbance units) |
|---|---|---|---|
| Control | | 24 h | 0.015 |
| M 3/14 | 8 | 3 h | 0.087 |
| M 3/14 | 8 | 24 h | 0.074 |
| M 3/14 | 20 | 3 h | 0.129 |
| M 3/14 | 20 | 24 h | 0.129 |
| M 3/14 | 20 | 72 h | 0.015 |

The experiment was conducted on an average of three individual animals per dose per time point. The brains were removed and extracted in dimethylformamide for 244 hrs. at room temp. The extract was centrifuged and the supernatant collected and measured for absorbance at 620 nm. The results are presented per gram wet weight of the tissue.

Lack of General Toxicity

No change of behavior was observed in the treated rats (in the 24 h experiment). Moreover, no brain edema or general edema was observed after 24 h in rats and in mice, as summarized in Tables 4 and 5. The $LD_{50}$ of M3/14 after intravenous administration to mice is between 150 mg/kg and 175 mg/kg.

TABLE 4

Effect of intra-arterial administration of M 3/14 on water concentration in the rat brain

| Group | Brain weight, g | After drying, g | Water, % |
|---|---|---|---|
| Control | 1.523 | 0.320 | 78.99 |
| M 3/14, 20 μg/ml, 24 h | 1.494 | 0.311 | 79.19 |

According to the results, there was no significant difference between the water content of the treated and non treated rats. These results indicate that there is no cerebral edema effect in response to M 3/14 infusion.

The rats were treated by intraarterial infusion of M 3/14 20 μg/ml or phosphate buffered saline as control. After 24 hours the rats were decapitated, the brain was removed and dried at 110° C. until constant weight was achieved (normally three days). The percent water was calculated by the following equation:

% water=(wet sample weight-dry sample weight)×100/(wet sample weight)

This procedure is according to Karpiak and Mahadik (1984, J. Neurosci. Res. 12, 485–492).

An acute intravenous toxicity test was performed to study the toxicity of the branched fatty acids in mice. The study included mortality and behavioral observations during three days. The rate of mortality is represented in the Table 5. M 3/14 caused mortality at a dose of 175 mg/kg; M3/12 at a dose of 75 mg/kg and M 3/10 at a dose of 100 mg/kg. Death was observed ten minutes after i.v. injection. In sub-lethal doses no significant behavior changes were observed.

TABLE 5

Acute toxicity test after intravenous administration of branched chain fatty acids into mice

| M molecule | Dose | Concentration | Mortality |
|---|---|---|---|
| M 3/14 | 50 mg/kg | 5 mg/ml | 0/3 |
| M 3/14 | 100 mg/kg | 5 mg/ml | 0/3 |
| M 3/14 | 150 mg/kg | 10 mg/ml | 0/3 |
| M 3/14 | 175 mg/kg | 10 mg/ml | 3/3 |
| M 3/12 | 50 mg/kg | 2.5 mg/ml | 0/3 |
| M 3/12 | 75 mg/kg | 2.5 mg/ml | 3/3 |
| M 3/10 | 50 mg/kg | 10 mg/ml | 0/3 |
| M 3/10 | 100 mg/kg | 10 mg/ml | 3/3 |

Lack of Neurotoxicity

Potential neurotoxicity after treatment with M 3,14 was assessed by means of histopathology on fixed sectioned rodent brains. The sections verified that there was no treatment related changes observed in the specimens.

Materials and Methods

Nine rodent brains were fixed in 10% neutral buffered formalin. These brains were obtained from rats infused with either buffer, 20 μg/ml, or 200 μg/ml M3,14 via the left internal carotid artery. The experiment was terminated and the samples collected either 3 or 72 hr. post infusion. Specimen and group identification were as follows:

control: 3 hr (2), 72 hr (1);

20 mg/ml M3,14: 3 hr (1), 72 hr(2);

200 mg/ml M3,14: 3 hr(1), 72 hr (2)

Upon receipt, coronal sections were prepared through the forebrain, midbrain and hindbrain. The right-left orientation was identified by placing a small cut in the cortex on the right side of the section. The sections were embedded as a single block, processed routinely in paraffin, sectioned at five microns and stained with hematoxylin and eosin. Sections were evaluated qualitatively.

Results

The sections verified that there was uniform perfusion and fixation of the specimens. No treatment related changes were observed. This was confirmed by a peer review. (The pathology study was performed at Pathology Associates Int., Frederick, Md., U.S.)

III. Mechanisms and Kinetics of BBB Alterations— In Vitro Models

The aim of this study was to assess the kinetics and mechanisms of Blood Brain-Barrier (BBB) alterations in an in vitro model of the BBB, using the compound denoted M3,14, which is also referred to herein as DP-BFA. DP-BFA is an analog of valproic acid (M3,14 sodium salt) which is a branched chain fatty acid.

1. In Vitro Model of the BBB

The alterations in barrier function on bovine brain capillary endothelial cells in co-culture were investigated. To provide an "in vitro" system for studying brain capillary functions, a process of coculture was used that closely mimics the "in vivo" situation by culturing brain capillary endothelial cells on one side of a filter and astrocytes on the other (Dehouck, et al. (1992) J. Neurochemistry 58:1790–1797). Endothelial cells form a confluent monolayer in 12 days.

FIG. 1 shows a scheme of the coculture. Endothelial cells are cultured in the upper compartment on the filter and astrocytes in the lower compartment on the plastic of the Petri dish.

Under these conditions, endothelial cells retain all the endothelial markers (factor VIII—related antigen, non-thrombogenic surface, production of prostacyclin, angiotensin converting enzyme activity) and the characteristics of the blood-brain barrier (presence of tight junctions, paucity of pinocytotic vesicles, monoamine oxidase activity, γ-glutamyltranspeptidase activity).

2. Effect of DP-BFA on the Paracellular Permeability of the BBB In Vitro 2.1. Preparation of DP-BFA Two different time points were tested, namely 1 hr and 24 hrs of incubation with DP-BFA, and five different concentrations per time point: 0.04; 0.08; 0.16; 0.24; 0.32 mg/ml corresponding to 0.125; 0.25; 0.5; 0.75; $1 \times 10^{-3}$ M.

DP-BFA is a saturated branched chain fatty acid (sodium salt) in a white powder form, which is sensitive to light and atmospheric $CO_2$ and should be protected from moisture. DP-BFA is stored in a hermetically sealed dark vial filled with Argon at 5° C. for up to 3 months. The drug quantity was taken out the vial cap with a Teflon spatula. The compound was dissolved in sodium carbonate-sodium bicarbonate buffered saline solution adjusted to pH 8.8–9 at 37° C. A stock solution (12.8 mg/ml) was prepared and kept at 37° C. for 15 minutes. The solution was protected from light by covering it with aluminium foil. The stock solution appeacompletely transparent. The desired concentration of DP-BFA was obtained by diluting the stock solution with the buffer. The solutions were filtered through a 0.45 gm filter.

The DP-BFA solutions were kept at 37° C. in vials protected from light, for no more than 6 hours.

Stock solution of DP-BFA was added directly to the coculture medium (upper compartment) in order to obtain a dilution of 1:40.

2.2. Permeability Study

Permeability studies were carried out on the monolayer of endothelial cells, using two paracellular tracers: inulin-$^3$H and sucrose-$^{14}$C.

To obtain a concentration-dependent transport parameter, the clearance principle was used. For each time, the increment in cleared volume between successive sampling events was calculated by dividing the amount of transported solute by the donor chamber concentration. The total volume cleared at each point was calculated by summing the incremental cleared volumes up to the given time point:

$$Clearance(\mu l) = \frac{[C]_A X V_A}{[C]_L}$$

where $[C]_L$ is the initial luminal tracer concentration, $[C]_A$ the abluminal tracer concentration, and $V_A$ the volume of the abluminal chamber. During the 45-mim experiment, the clearance volume increased linearly with time. The average volume cleared was plotted versus time, and the slope was estimated by linear regression analysis to give the mean and the SE to the estimate. The slope of the clearance curves for the coculture was denoted $PS_t$, where PS is the permeability x surface area product (in microliters per minute). The slope of the clearance curve for the control filter was denoted $PS_f$.

The PS value for the endothelial monolayer ($PS_e$) was calculated from $$\frac{1}{PSe} = \frac{1}{PSt} - \frac{1}{PSf}$$

The $PS_e$ values were divided by the surface area of the Millicell-PC (4.2 cm$^2$) to generate the endothelial permeability coefficient ($P_e$, in centimeters per minute).

The permeability coefficient cannot be calculated when the clearance volume does not increase linearly with time. In that case, the results are presented as clearance ($\mu l$) in function of time (min) and clearance at 45 minutes for each condition.

2.2.1. Results

Figure 2A:
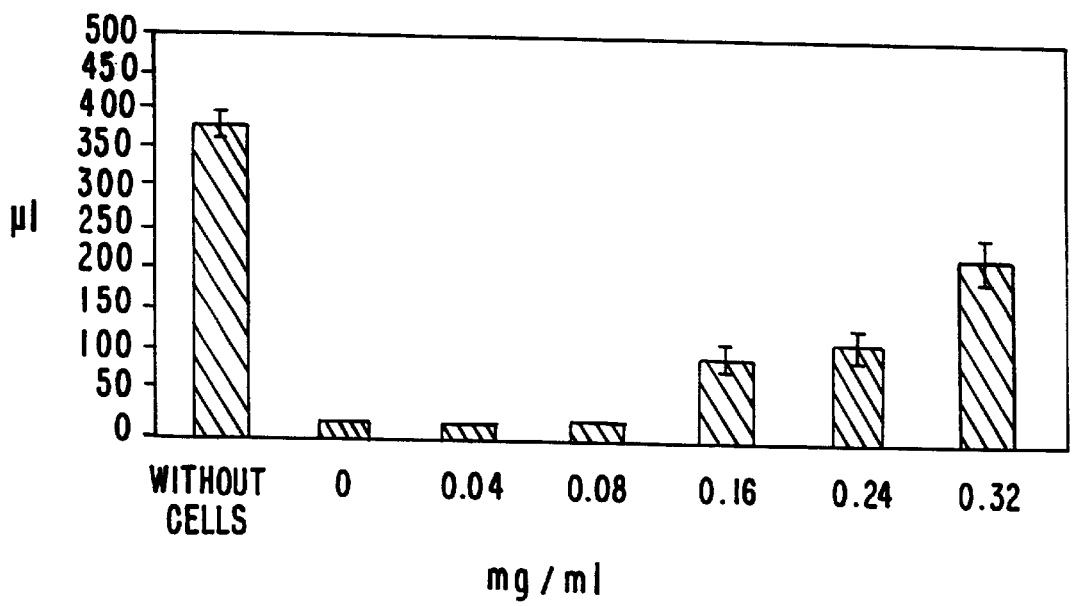
FIG. 2: Inulin and sucrose clearances ($\mu l$) at 45 minutes, after DP-BFA 1 hr
Figure 2B:
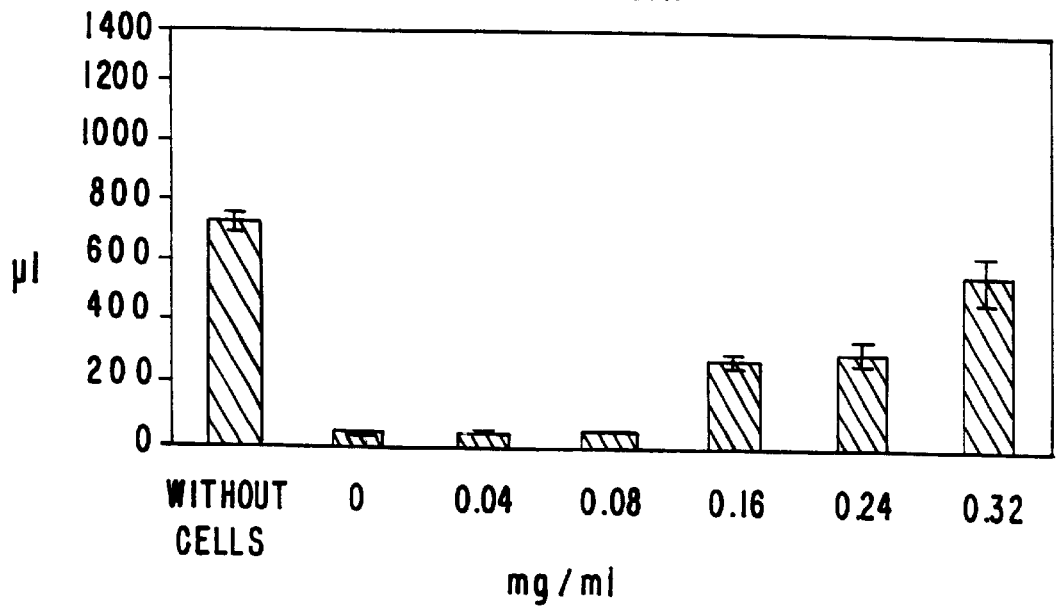
Figure 3A:
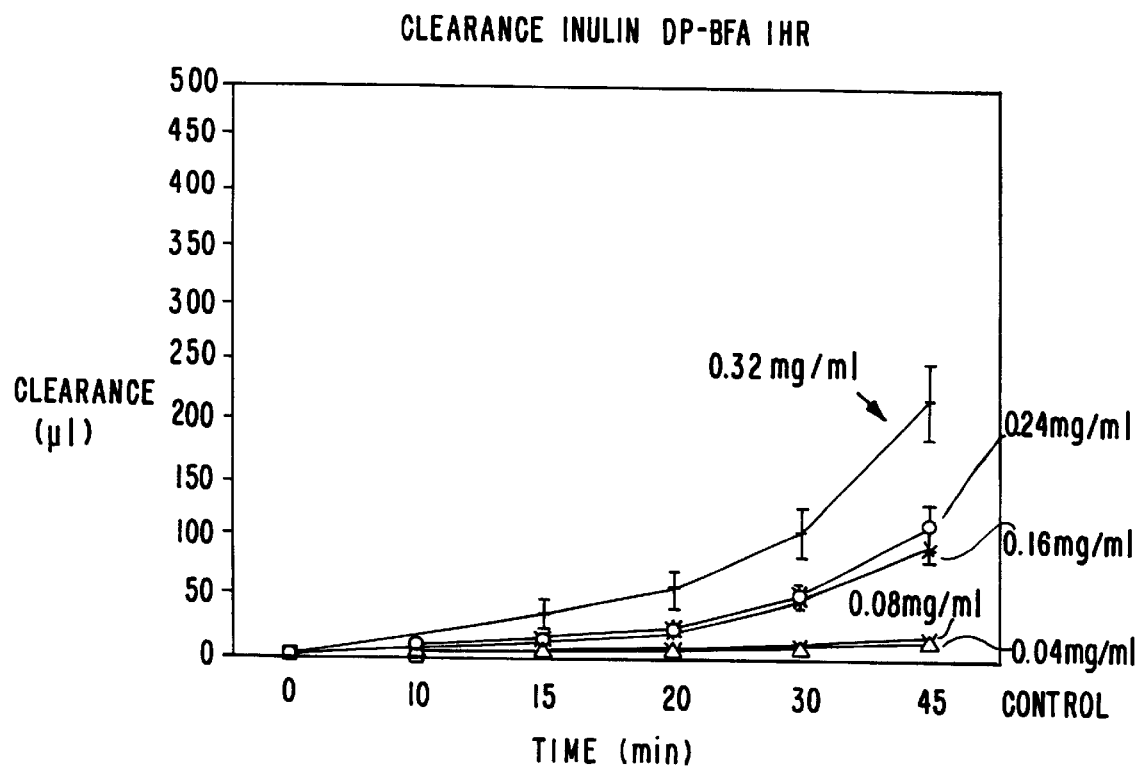
FIG. 3: Inulin and sucrose permeabilities, after DP-BFA 1 hr
Figure 3B:
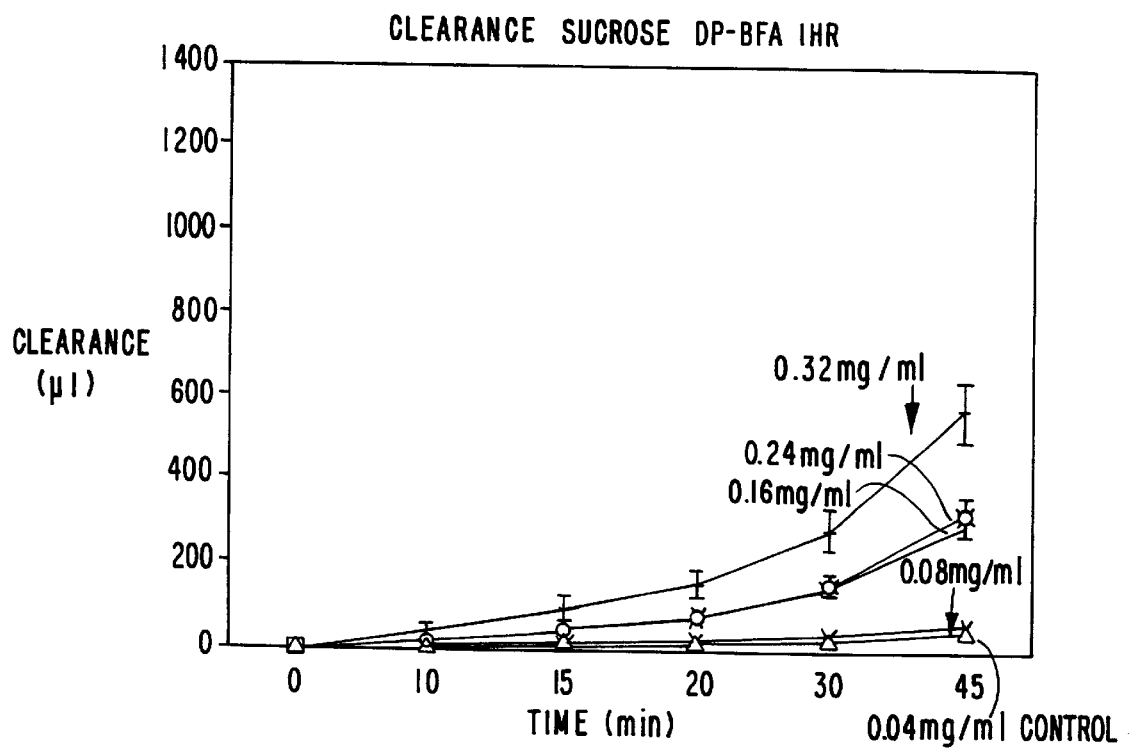
Figure 4A:
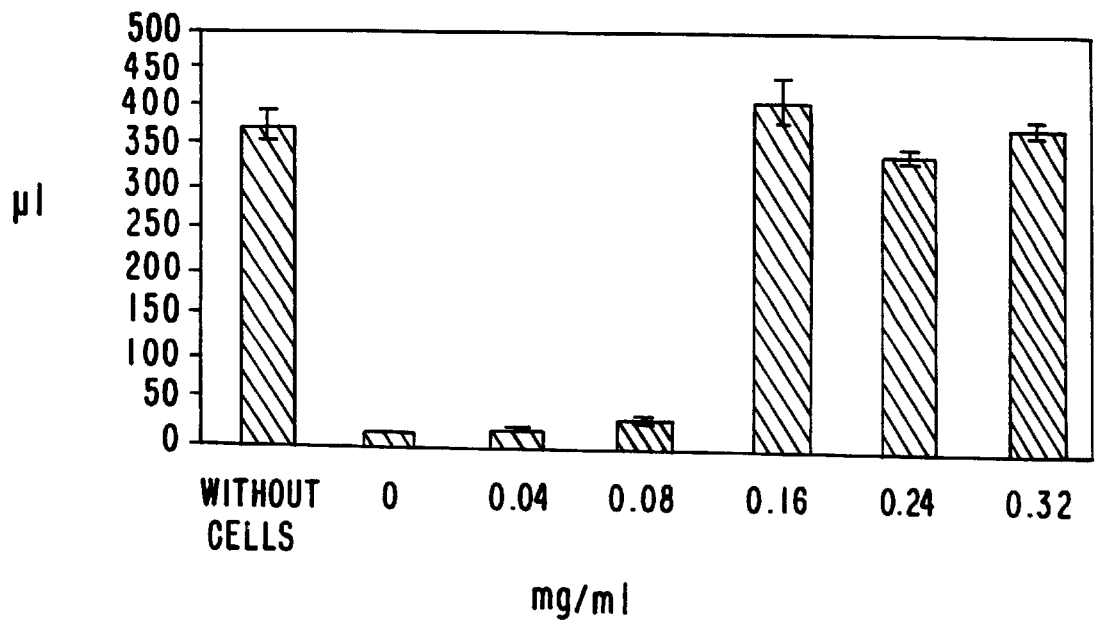
FIG. 4: Inulin and sucrose clearances ($\mu l$) at 45 minutes, after DP-BFA 24 hrs
Figure 4B:
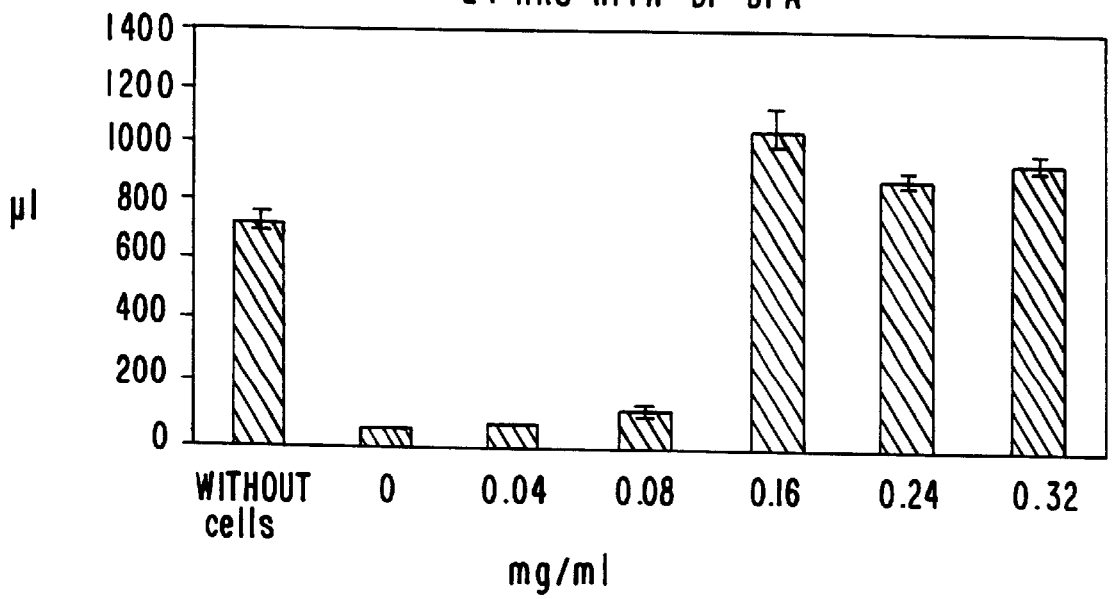

A significant increase was measured in the permeability of the monolayer (clearance at 45 minutes) for sucrose and inulin:

679% and 636% respectively at the concentration of 0.16 mg/ml after 1 hour incubation with DP-BFA, 199% and 179% respectively at the concentration of 0.08 mg/ml after 24 hours incubation with DP-BFA; (FIGS. 2, 3 and 4).

2.3. Actin Staining

To investigate the origin of this modification of the permeability, fluorescent microscopy studies were undertaken. Actin filaments were localized with bodipy phallo?din (explanations in section 7.1.).

2.3.1. Results

In control, a delicate network of actin filaments was observed mainly throughout the cytoplasm with preferentially cortical membrane associated actin.

Endothelial cells incubation 1 hr with 0.16 mg/ml DP-BFA, or 24 hrs with 0.08 mg/ml DP-BFA, exhibited an increase in numerous densely packed stress fibers. Endothelial cells stress fibers were associated with significant morphological changes.

Interendothelial cell gaps in the monolayer could be seen after 0.16 mg/ml DP-BFA, 24 hrs.

2.4. Determination of Lactate Dehydrogenase

In the same experiments, lactate dehydrogenase was assayed in the medium in order to check the toxicity.

This cytoplasmic enzyme is not able to cross the cellular membrane except if the membrane integrity is destroyed. An increase in the release of Lactate Dehydrogenase (LDH) indicates a breakdown of the cellular membrane, leading to a cellular death. In other words, the LDH determination in the medium allows an assessment of cell viability.

2.4.1. Results

Figure 5A:
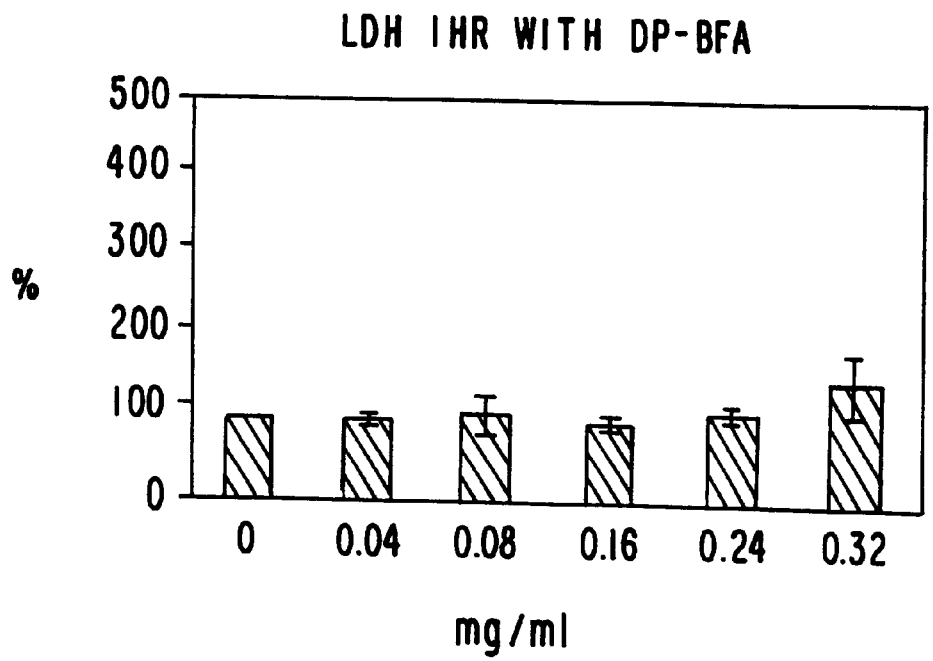
FIG. 5: Determination of LDH in the medium of endothelial cells in coculture
Figure 5B:
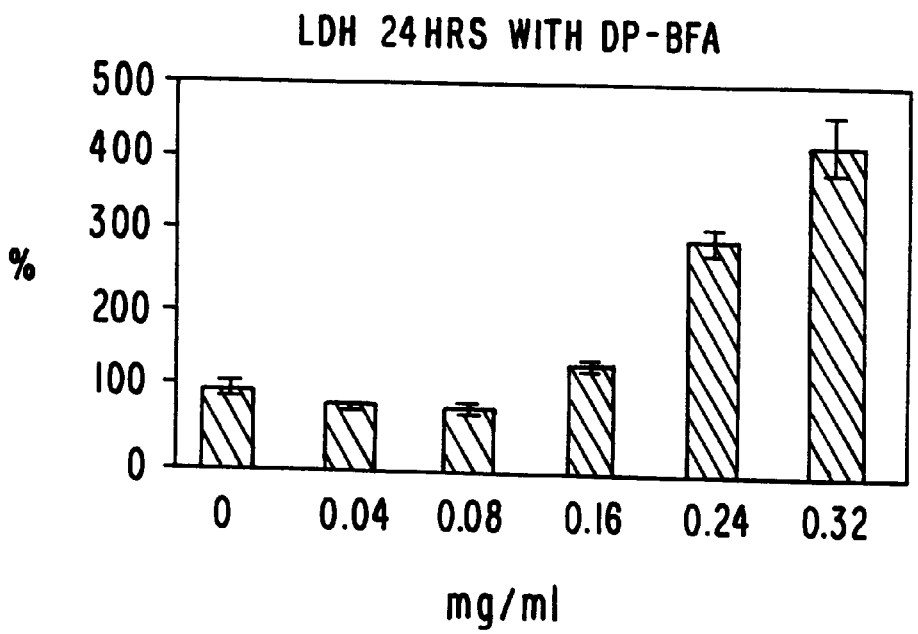

After one hour of incubation with DP-BFA no significant increase in LDH release was observed (FIG. 5a). A significant increase in LDH release was noted after 24 hrs incubation with 0.16 mg/ml DP-BFA, in the endothelial cells medium (FIG. 5b).

2.5. Conclusion

A cytotoxic effect of DP-BFA could be observed at 0.16 mg/ml concentrations after 24 hrs incubation on brain capillary endothelial cells in coculture with astrocytes (LDH release and interendothelial cell gaps).

A paracellular breakdown (opening of the tight junctions) was observed at the concentration of 0.16 mg/ml after 1 hr and 0.08 mg/ml after 24-hrs incubation with DP-BFA, associated with the rearrangement of the cytoskeletal architecture.

3. Effect of DP-BFA on the Transcellular Permeability of the BBB In Vitro 3.1. Preparation of DP-BFA 1 hr incubation with the test material and five different concentrations: 0.04; 0.08; 0.16; 0.24; 0.32 mg/ml corresponding to 0.125; 0.25; 0.5; 0.75; $1\times10^{-3}$ M, were chosen for this experiment.

Stock solution of DP-BFA was added directly to the coculture medium (upper compartment) in order to obtain a dilution of 1:40.

3.2. Permeability Study

Permeability studies was carried out on the monolayer of endothelial cells using a transcellular tracer: albumin-FITC (fluorescein isothiocyanate), MW=66500. There is no albumin receptor on endothelial cells. Albumin crossed the monolayer by a non-specific transport.

To obtain a concentration-dependent transport parameter, the clearance principle was used like sucrose or inulin (see paragraph 2.2.).

Albumin-FITC was used on endothelial cells at the concentration of 100 µg/ml in Ringer-Hepes 0.4% albumin.

The fluorescence of each sample was determined at λ.excitation of 495 and λ.emission of 525 using a fluorescence spectrophotometer F-2000 (Hitachi).

The permeability coefficient can not be calculated when the clearance volume does not increase linearly with time. In that case, the results are presented as clearance (µl) in function of time (min) and clearance at 180 minutes for each condition.

3.2.1. Results

Figure 6A:
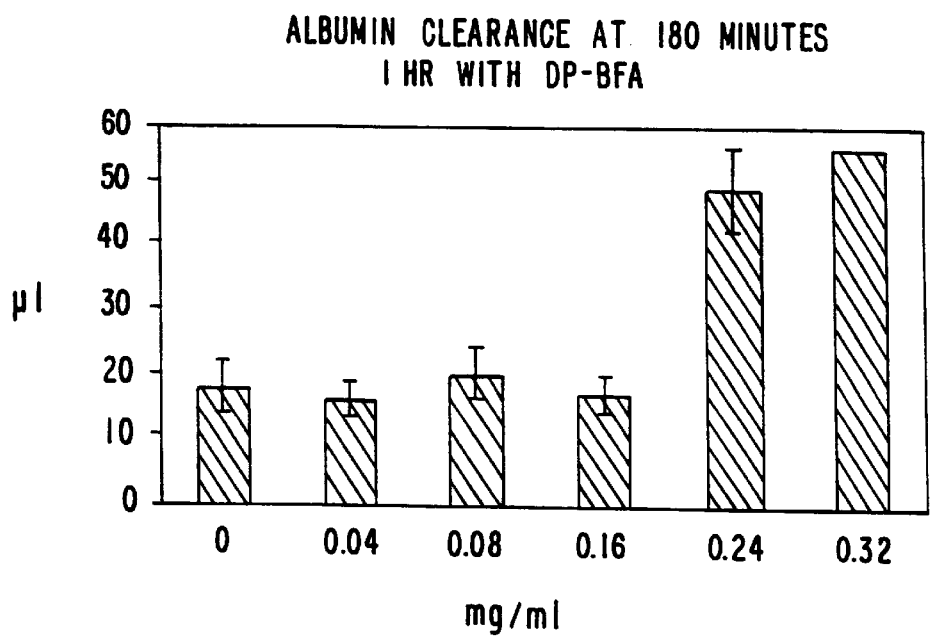
FIG. 6: Albumin permeability
Figure 6B:
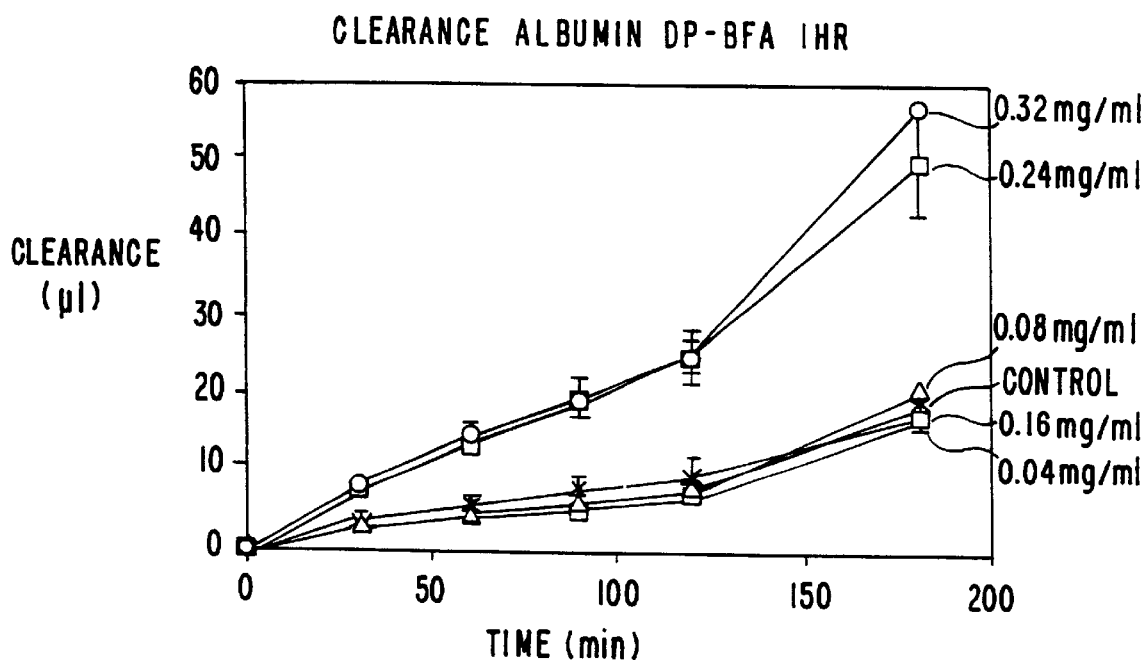

A significant increase was obtained in the permeability of the monolayer for albumin (clearance at 180 minutes): 268% at the concentration of 0.24 mg/ml after 1-hour incubation with DP-BFA (FIG. 6).

3.3. Determination of Lactate Dehydrogenase

In the same experiments, lactate dehydrogenase was assayed in the medium, in order to check the toxicity.

3.3.1. Results

Figure 7:
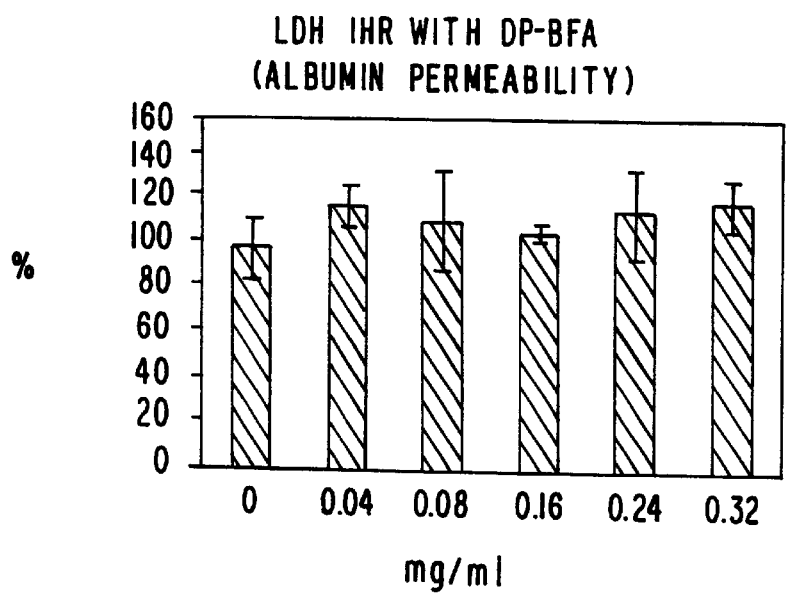
FIG. 7: Determination of LDH in the medium of endothelial cells in coculture

No increase in release of LDH could be detected in the incubation medium of endothelial cells with DP-BFA after 1 hr incubation (FIG. 7).

3.4. Conclusion

No cytotoxic effect of DP-BFA could be observed at the tested concentration on brain capillary endothelial cells in cocultute with astrocytes after 1 hr incubation with DP-BFA.

However, a 2.7 fold increase of non-specific transcellular transport was observed at the concentration of 0.24 mg/ml after lhr incubation with DP-BFA.

4. Reversibility of DP-BFA Effect on the Paracelllular Permeability of the BBB In Vitro 4.1. Preparation of DP-BFA In regard with the previous results, 0.16 mg/ml (paracellular opening after 1 hr) and 0.32 mg/ml (paracellular and transcellular openings after 1 hr) were chosen to study the reversibility of the effect of DP-BFA.

The following protocol was used:

Endothelial cells are cocultured 12 days, on the twelfth culture day DP-BFA was added to the cultures for 1 hour, and then removed by replacement of the culture medium. The cultures then were maintained for a further 24 hours without DP-BFA, and subsequently assayed for paracellular permeability.

4.2. Permeability Study

Permeability studies were carried out on the monolayer of endothelial cells, using two paracellular tracers: inulin-$^3$H and sucrose-$^{14}$C.

4.2.1. Results

Figure 8:
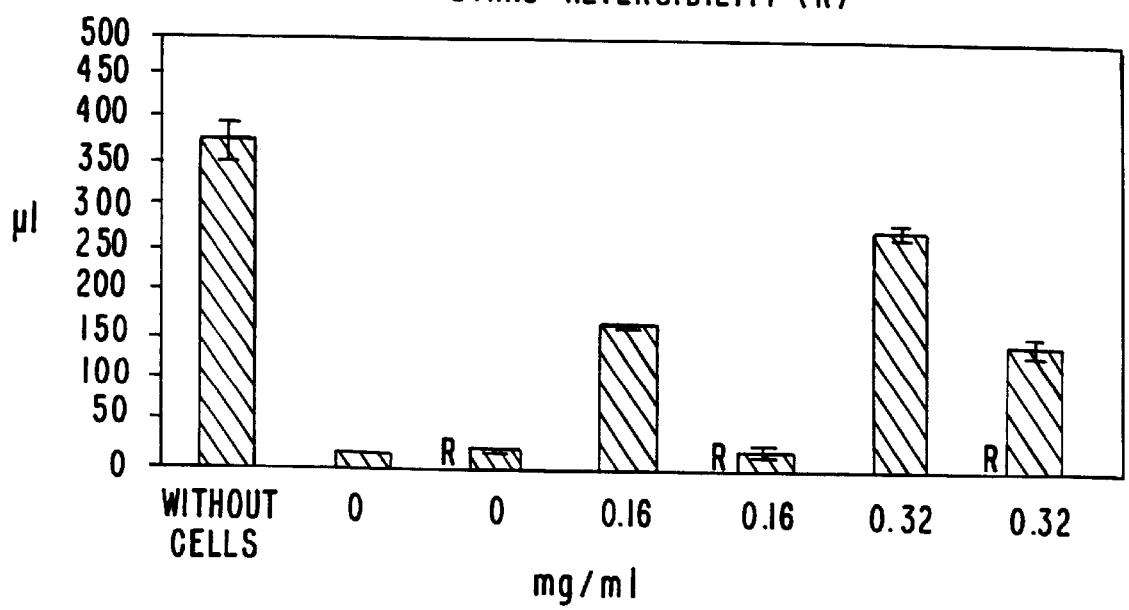
FIG. 8: Inulin clearance ($\mu l$) at 45 minutes, after 24 hrs reversibility

As already noted, an increase in the permeability of the monolayer for sucrose and inulin at the concentration of 0.16 mg/ml and 0.32 mg/ml after 1 hour incubation with DP-BFA was observed (FIGS. 8 and 9).

But, after washing and incubating endothelial cells 24 hrs with fresh medium in presence of astrocytes, we observed a complete reversibility of the paracellular permeability (clearance at 45 minutes) at 0.16 mg/ml DP-BFA and only a decrease of 50% for 0.32 mg/ml DP-BFA (FIGS. 8 and 9).

4.3. Actin Staining 4.3.1. Results

In control, a delicate network of actin filaments was observed mainly throughout the cytoplasm with preferentially cortical membrane associated actin.

Endothelial cells after 0.16 mg/ml DP-BFA, 1 hr exhibited an increase in numerous densely packed stress fibers. Endothelial cells stress fibers were associated with significant morphological changes.

After 24 hrs without DP-BFA, endothelial cells morphology did not change but there were less densely packed stress fibers.

4.4. Determination of Lactate Dehydrogenase

In the same experiments, lactate dehydrogenase was assayed in the medium, in order to check the toxicity.

4.4.1. Results

Figure 10A:
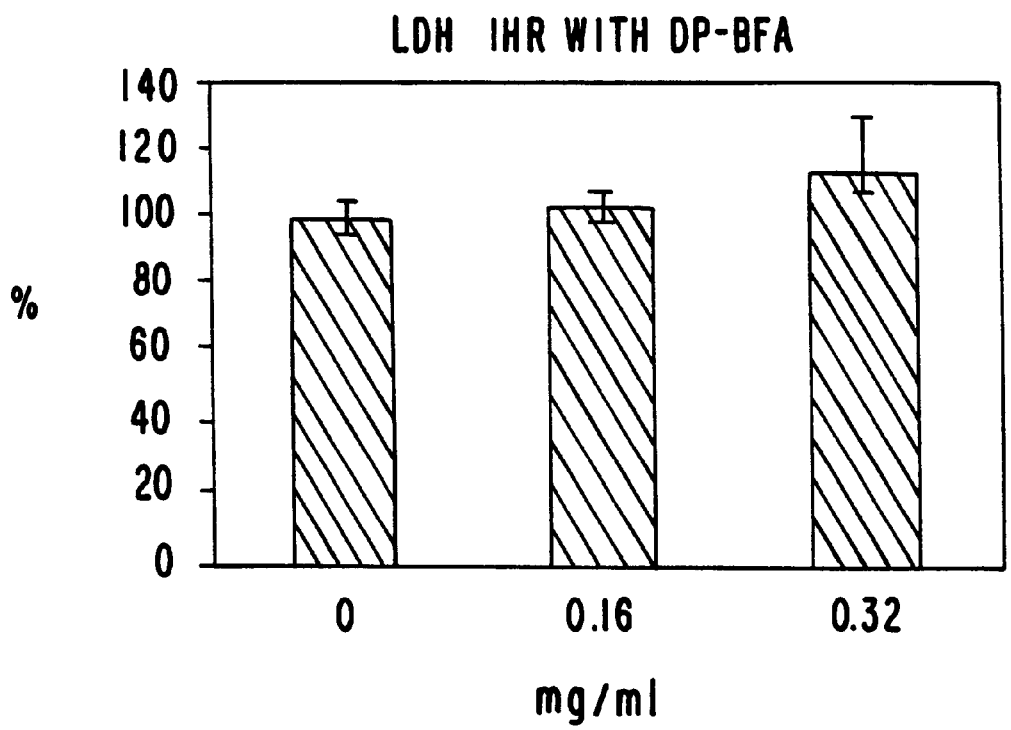
FIG. 10: Determination of LDH in the medium of endothelial cells in coculture
Figure 10B:
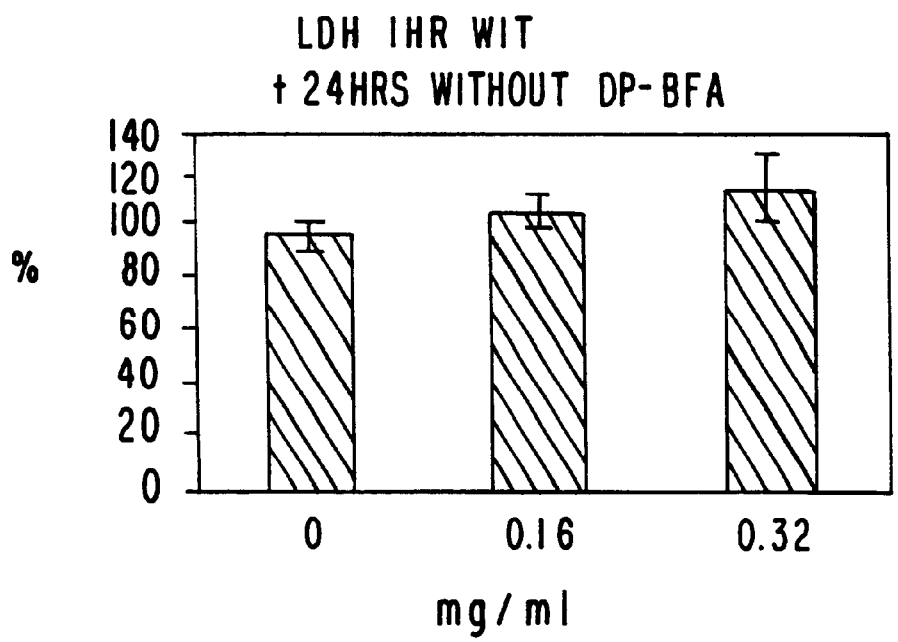

No increase in release of LDH could be detected in the incubation medium of endothelial cells with DP-BFA and after the 24 hrs reversibility study (FIG. 10).

4.5. Conclusion

No cytotoxic effect of DP-BFA could be observed at the tested concentration on brain capillary endothelial cells in coculture with astrocytes.

A paracellular breakdown (opening of the tight junctions) was noted at the concentration of 0.16 mg/ml and 0.32 mg/ml after 1 hr incubation with DP-BFA. But a complete reversibility of DP-BFA effect was only observed for the concentration of 0.16 mg/ml after 24 hrs without DP-BFA, associated with stress fibers decrease.

5. Reversibility Kinetic of DP-BFA Effect on the Paracellular Permeability of the BBB In Vitro 5.1. Preparation of DP-BFA In view of the previous results, 0.16 mg/ml (which demonstrated paracellular opening after 1 hr) was chosen to study the kinetics of reversibility of the effect of DP-BFA.

The following protocol was used:

Endothelial cells are cocultured 12 days, and on the twelfth day DP-BFA was added to the cultures for one hour. The cultures were then washed to remove the test material and cultured for a further period of 3, 6 or 18 hours without DP-BFA.

5.2. Permeability Study

Permeability studies were carried out on the monolayer of endothelial cells, using two paracellular tracers: inulin-$^3$H and sucrose-$^{14}$C.

5.2.1. Results

Figure 11:
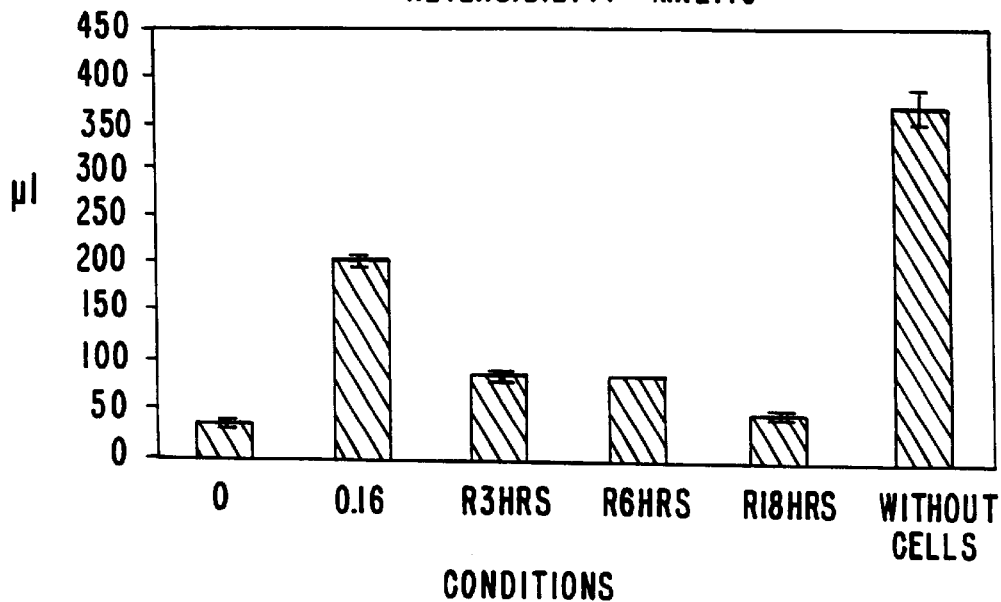
FIG. 11: Inulin clearance (μl) at 45 minutes, reversibility kinetics
Figure 12:
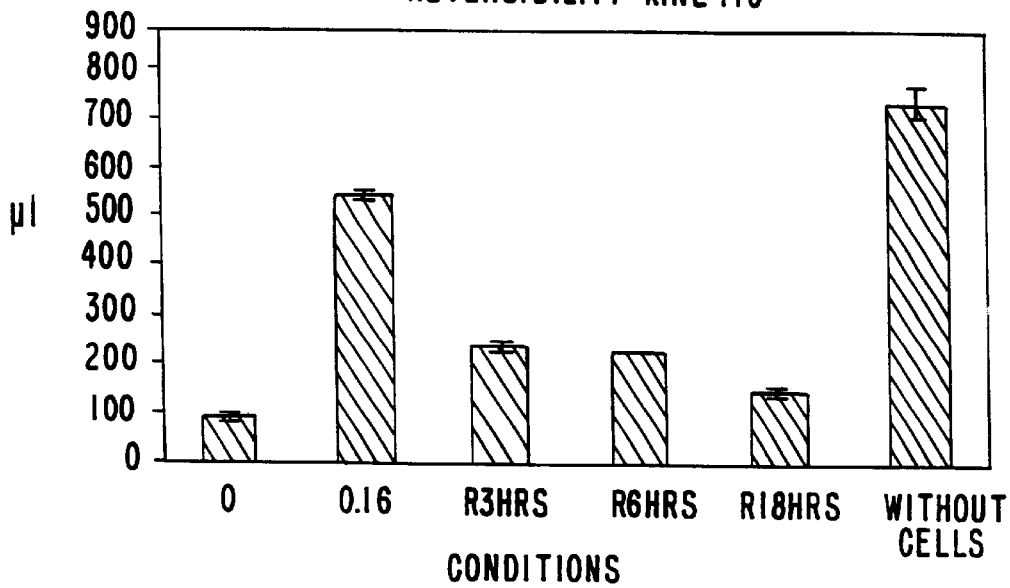
FIG. 12: Sucrose clearance (μl) at 45 minutes, reversibility kinetics

As already noted, an increase in the permeability of the monolayer for sucrose and inulin at the concentration of 0.16 mg/ml after 1 hour incubation with DP-BFA as observed (FIGS. 11 and 12).

But, after washing and incubating endothelial cells for 3, 6 and 18 hrs with fresh medium in the presence of astrocytes, a decrease in paracellular permeability was observed (expressed as clearance at 45 minutes): of 58%, 58% and 76% for inulin and 56%, 57% and 72% for sucrose, respectively (FIGS. 11 and 12).

5.3. Determination of Lactate Dehydrogenase

In the same experiments, lactate dehydrogenase was assayed in the medium, in order to check the toxicity.

5.3.1. Results

No increase in release of LDH could be detected in the incubation medium of endothelial cells with DP-BFA or after reversibility kinetic study (FIG. 13).

5.4. Conclusion

No cytotoxic effect of DP-BFA could be observed at the tested concentration on brain capillary endothelial cells in coculture with astrocytes.

A paracellular breakdown (opening of the tight junctions) was noted at the concentration of 0.16 mg/ml after 1 hr incubation with DP-BFA. But an incomplete reversibility of DP-BFA effect was observed after 3, 6 and 18 hrs.

6. General Conclusion

A paracellular breakdown (opening of the tight junctions) was observed at the concentration of 0.16 mg/ml after 1 hr and 0.08 mg/ml after 24 hrs incubation with DP-BFA. The modification of the transport of these molecules could be associated with the rearrangement of the cytoskeletal architecture:

increase in numerous densely packed stress fibers, significant morphological changes.

A cytotoxic effect of DP-BFA could only be observed after 24 hrs incubation at 0.16 mg/ml concentrations on endothelial cells in coculture with astrocytes. No cytotoxic effect was observed after 1 hour incubation, as determined by the increase in LDH release.

An increase of non-specific transcellular transport was observed only at higher concentration (0.24 mg/ml after 1 hr incubation with DP-BFA), and was not associated with cytotoxic effects.

A complete reversibility was observed for the concentration of 0.16 mg/ml after 24 hrs without DP-BFA. Partial reversibility was observed using higher concentrations of DP-BFA.

One of the major findings is that the effect of the drug is reversible. A preliminary kinetic study shows that even after 3 hours, a decrease in the paracellular transport could be observed.

8 Methods 8.1. Actin Staining

Fixation

The medium was removed and filter-grown endothelial cells were washed gently twice with Ringer-Hepes buffer.

Filter-grown endothelial cells were fixed in 4% PAF (paraformadehyde, in PHS buffer supplemented with $MgCl_2$, 2 mM and EGTA, 10 mM) for 15 min at 4° C.

PAF was removed and filter-grown endothelial cells were washed once with PHEMS buffer. The filter-grown endothelial cells can be stored in PHEMS buffer at 4° C.

Permeabilizing

The filter-grown endothelial cells were cut up in eight pieces in a large PHEMS buffer drop and stored in PHEMS. One piece was permeabilized with acetone at −20° C. for 1 min then stored in PHEMS buffer.

Fluorescent Staining

Actin filaments were localized with bodipy phallo?din (Molecular Probes, Inc.). The stain was dissolved in 1.5 ml of methanol (200 units/ml) but was used at 5 units/ml. 5 μl of stock solution was evaporated and redissolved in 200 μl of PHS buffer.

⅛ of permeabilized filter-grown endothelial cells was covered with 25 to 50 μl of stain solution, 30 min at room temperature in darkroom. The filter bearing the endothelial cells was rinsed twice with PHEMS buffer, once with water.

The filter-grown endothelial cells were mounted cell-side up on a microscope slide in mowiol. And was examined on a Leitz DMR microscope using oil immersion objectives.

| 8.2. BUFFER SOLUTIONS | | |
|---|---|---|
| PHS buffer: | Hepes | 25 mM |
|  | Pipes | 60 mM |
|  | NaCl | 0.15 M |
| PHEMS buffer: | PHS buffer |  |
|  | +$MgCl_2$ | 2 mM |
|  | +EGTA | 10 mM |
| RINGER HEPES: | pH 7.4 |  |
|  | NaCL | 150 mM |
|  | KCl | 5.2 mM |
|  | $CaCl_2$ | 2.2 mM |
|  | $MgCl_2$, $6H_2O$ | 0.2 mM |
|  | $NaHCO_3$ | 6 mM |
|  | Hepes | 5 mM |
|  | Glucose | 2.8 mM |

IV. In Vivo Efficacy Studies

In order to test the efficacy of the methods according to the present invention, experiments were designed to test the effect of permeabilization of the BBB in facilitating the penetration of drugs into the central nervous system, in a clinically relevant situation, namely in rats bearing CNS tumors.

Scientific Method

In this experiment five groups of Fischer rats (n=15) are used. In each group malignant brain tumors are induced by intracerebral stereotactic implanatation of malignant brain tumor cells (9L Gliosarcoma cells). In the first group the rats receive M3, 14 and chemotherapy intra-arterially. In group two rats receive M3, 14 intra-arterially and the chemotherapy intravenously. Group three the rats receive saline and chemotherapy intra-arterially. In group four the rats receive only chemotherapy intravenously. The fifth group is the untreated control group. The table below summarizes succintly the information listed above.

| GROUP | SUBSTANCE | DELIVERY |
|---|---|---|
| 1 | M3, 14 Chemo | IV |
| 2 | M3, 14 + Chemo | IA |
| 3 | Saline + Chemo | IA |
| 4 | Chemo | IV |
| 5 | Null | Null |

Tissue Cultures

Fischer rat 9L gliosarcoma cells are propagated in T-175 tissue culture flasks in Dulbeccos modified Eagles (DMEM) with 10% fetal bovine serum, 2 mM L-glutamine, 50 units/ml pencillin, 50 micrograms/ml of streptomucin, and 2.5 micrograms/ml of fungizone.

Surgical Procedure and Drug Administration

The Fischer rats, weighing 250–300 grams, are anesthetized with intra-peritoneal ketamine (90 mg/kg) and xylazine (10 mg/kg) and then placed in a stereotactic apparatus (David Kopf Instrutments). The 9L gliosarcoma cells (40000 cells in a 5 microliter Hanks balanced salt solution) are stereotactically injected into the deep white matter of the right frontal lobe. Ten days after the implanatation the rats are anesthesized and cartoid artery cannulation is performed. One ml of M3, 14 is administered with the chemotherapeutic drug. The chemotherapeutic agent used is cis-platinuim (a second generation analogue of cis, a DNA intercalating genes). Please refer to the table above which shows which groups of rats will receive cis-platinium I.V. or I.A. The compound M3, 14 when given, is always in the intra-arterial route.

Statistical Analysis

The main parameter examined is the survival time for each group using the Kaplan Meir survival curves. The question analyzed is whether rats injected with the chemotherapeutic substance, i.e., cis-platinium after administration of the test compound M3, 14 have statistically significantly prolonged survival times compared to control rats.

Preliminary Studies

Preliminary studies have been performed in order to ascertain whether administration of M3,14 can be demonstrated to facilitate the entry of chemotherapeutic agents into the central nervous system. In this study M3,14 was administered intra-arterially, into the carotid artery, and the agent methotrexate was administered into the same artery. The content of methotrexate in the ipsilateral hemisphere of the brain was quantitated as a function of time, in three groups: control animals, animals pretreated with M3,14 and animals pretreated with mannitol. As presented in Table 6, it is apparent that the pre-treatment with M3,14 significantly increased the penetration of MTX into the ipsilateral hemisphere of the brains.

TABLE 6

Methotrexate content of brains of rats pretreated with M3,14 (DP-BFA)

| Time (min) | ipsilateral, control | ipsilateral, 3,14-BFA Na (40 μg/ml) |
|---|---|---|
| 0 | 0 | 0.005 |
| 30 | 0.027 | 0.036 |
| 60 | 0.049 | 0.26 |
| 90 | 0.095 | 0.41 |
| 120 | 0.095 | 0.41 |

TABLE 6-continued

Methotrexate content of brains of rats pretreated with M3,14 (DP-BFA)

| Time (min) | ipsilateral, control | ipsilateral, 3,14-BFA Na (40 μg/ml) |
|---|---|---|
| 150 | 0.109 | 0.7 |
| 180 | 0.19 | 0.7 |
| 210 | 0.218 | |

What is claimed is:

1. A method of enhancing permeabilization of a biological membrane comprising exposing the membrane to a compound of the general formula III:

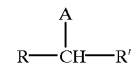

(III)

wherein R denotes a saturated or unsaturated chain of between 1 to 10 carbon atoms and R' denotes a saturated or unsaturated chain of between 5 and 30 carbon atoms, and A is selected from the group consisting of COOH, COOR", CONH$_2$, CONH—R", and COO$^-$Y$^+$ wherein R" is a lower alkyl group comprising 1–5 carbon atoms, and Y denotes any pharmaceutically acceptable counter-ion.

2. The method according to claim 1 wherein in the compound of the general formula III, R is propyl and R' is decanoyl.

3. The method according to claim 1 wherein in the compound of the general formula III, R is propyl and R' is dodecanoyl.

4. The method according to claim 1 wherein in the compound of the general formula III, R is propyl and R' is tetradecanoyl.

5. The method according to claim 1 wherein in the compound of the general formula III, R and R' are each heptyl.

6. The method according to claim 1 wherein in the compound of the general formula III, R is heptyl and R' is decanoyl.

7. The method according to claim 1 wherein in the compound of the general formula III, R is heptyl and R' is tetradecanoyl.

8. The method according to claim 1 wherein in the compound of the general formula III, R and R' are each decanoyl.

9. The method according to claim 1 wherein in the compound of the general formula III, R is decanoyl and R' is tetradecanoyl.

10. A method of reversibility permeabilizing a biological membrane comprising exposing the membrane to a compound of the general formula II.

11. A method of reversibility permeabilizing a biological membrane comprising exposing the membrane to a compound of the general formula III.

12. A method of reversibly permeabilizing a biological membrane which comprises administering to a mammal a compound of the general formula II.

13. A method of reversibly permeabilizing a biological membrane which comprises administering to a mammal a compound of the general formula III.

14. A method of treating CNS lesions or diseases comprising: administering to a subject in need thereof a pharmaceutical composition comprising a pharmaceutically effective amount of a compound of the general formula II or III as heretofore defined; and subsequently administering a therapeutic agent within 24 hours.

15. The method of claim 14 further comprising administering the compound intravenously or intra-arterially.

16. A method of enhancing permeabilization of a biological membrane comprising exposing the membrane to a compound of the general formula II:

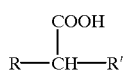

(II)

wherein R denotes a saturated or unsaturated chain of between 1 to 10 carbon atoms and R' denotes a saturated or unsaturated chain of between 5 and 30 carbon atoms, their salts, esters and amides.

17. The method according to claim 16 wherein in the compound of the general formula II, R is propyl and R' is decanoyl.

18. The method according to claim 16 wherein in the compound of the general formula II, R is propyl and R' is dodecanoyl.

19. The method according to claim 16 wherein in the compound of the general formula II, R is propyl and R' is tetradecanoyl.

20. The method according to claim 16 wherein in the compound of the general formula II, R and R' are each heptyl.

21. The method according to claim 16 wherein in the compound of the general formula II, R is heptyl and R' is decanoyl.

22. The method according to claim 16 wherein in the compound of the general formula II, R is heptyl and R' is tetradecanoyl.

23. The method according to claim 16 wherein in the compound of the general formula II, R and R' are each decanoyl.

24. The method according to claim 16 wherein in the compound of the general formula II, R is decanoyl and R' is tetradeanoyl.

25. A pharmaceutical composition for the permeabilization of biological membranes comprising a pharmaceutically effective amount of a compound of the general formula:

wherein R denotes a saturated or unsaturated chain of between 4 to 10 carbon atoms and R' denotes a saturated or unsaturated chain of between 5 and 30 carbon atoms, and A is selected from the group consisting of COOR", CONH$_2$, CONH—R", and COO$^-$Y$^+$ wherein R" is a lower alkyl group comprising 1–5 carbon atoms, and Y denotes any pharmaceutically acceptable counter-ion; and, at least one pharmaceutically acceptable carrier.

26. The pharmaceutical composition according to claim 25 wherein R and R' are each heptyl.

27. The pharmaceutical composition according to claim 25 wherein R is heptyl and R' is decanoyl.

28. The pharmaceutical composition according to claim 25 wherein R is heptyl and R' is tetradecanoyl.

29. The pharmaceutical composition according to claim 25 wherein R and R' are each decanoyl.

30. The pharmaceutical composition according to claim 25 wherein R is decanoyl and R' is tetradecanoyl.

31. A method of reversibly permeabilizing a biological membrane comprising exposing the membrane to the pharmaceutical composition of claim 25.

32. A method of reversibly permeabilizing a biological membrane which comprises administering to a mammal the pharmaceutical composition of claim 25.

33. The pharmaceutical composition according to claim 25 wherein R" is a lower alkyl group comprising 2–5 carbon atoms.

34. A method of improving CNS imaging comprising: administering to a subject in need thereof a pharmaceutical composition comprising a pharmaceutically effective amount of a compound of the general formula II or III as heretofore defined; and subsequently administering a therapeutic agent within 24 hours.

35. The method of claim 34 further comprising administering the compound intravenously or intra-arterially.

36. A pharmaceutical composition for the permeabilization of biological membranes comprising a compound of the general formula:

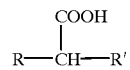

wherein R denotes an unsaturated chain of between 4 to 10 carbon atoms and R' denotes a saturated or unsaturated chain of between 5 and 30 carbon atoms, their salts, esters and amides; and, at least one pharmaceutically acceptable carrier.

37. A method of reversibly permeabilizing a biological membrane comprising exposing the membrane to the pharmaceutical composition of claim 36.

38. A method of reversibly permeabilizing a biological membrane which comprises administering to a mammal the pharmaceutical composition of claim 36.

39. A pharmaceutical composition for the permeabilization of biological membranes comprising a compound of the general formula:

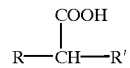

wherein R denotes a saturated chain of between 4 to 10 carbon atoms and R' denotes an unsaturated chain of between 5 and 30 carbon atoms, their salts, esters and amides; and, at least one pharmaceutically acceptable carrier.

40. A method of reversibly permeabilizing a biological membrane comprising exposing the membrane to the pharmaceutical composition of claim 39.

41. A method of reversibly permeabilizing a biological membrane which comprises administering to a mammal the pharmaceutical composition of claim 39.

42. A pharmaceutical composition for the permeabilization of biological membranes comprising a compound of the general formula:

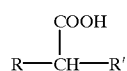

wherein R denotes a saturated chain of between 4 to 10 carbon atoms and R' denotes a saturated chain of between 25 and 30 carbon atoms, their salts, esters and amides; and, at least one pharmaceutically acceptable carrier.

43. A method of reversibly permeabilizing a biological membrane comprising exposing the membrane to the pharmaceutical composition of claim 42.

44. A method of reversibly permeabilizing a biological membrane which comprises administering to a mammal the pharmaceutical composition of claim 42.

* * * * *